(12) United States Patent
Shelton, IV et al.

(10) Patent No.: US 8,357,088 B2
(45) Date of Patent: Jan. 22, 2013

(54) METHODS AND DEVICES FOR PROVIDING ACCESS INTO A BODY CAVITY

(75) Inventors: Frederick E. Shelton, IV, Hillsboro, OH (US); Jerome R. Morgan, Cincinnati, OH (US); Theodore R. Farrell, Penfield, NY (US)

(73) Assignee: Ethicon Endo-Surgery, Inc., Cincinnati, OH (US)

(*) Notice: Subject to any disclaimer, the term of this patent is extended or adjusted under 35 U.S.C. 154(b) by 304 days.

(21) Appl. No.: 12/635,762

(22) Filed: Dec. 11, 2009

(65) Prior Publication Data

US 2011/0144448 A1 Jun. 16, 2011

(51) Int. Cl.
*A61B 1/32* (2006.01)
*A61B 17/34* (2006.01)
(52) U.S. Cl. ................ 600/215; 604/108; 606/198
(58) Field of Classification Search .......... 600/201–206, 600/208–219, 224–234; 606/107–109, 167, 606/170, 184–185, 193–194, 198, 323; 604/95.02, 604/288.01–288.03, 513, 264, 506, 164.1, 604/164.11, 106–108
See application file for complete search history.

(56) References Cited

U.S. PATENT DOCUMENTS

| | | | |
|---|---|---|---|
| 3,397,699 A | 8/1968 | Kohl | |
| 3,924,632 A * | 12/1975 | Cook | 604/527 |
| 4,022,191 A | 5/1977 | Jamshidi | |
| 4,608,977 A | 9/1986 | Brown | |
| 4,809,694 A | 3/1989 | Ferrara | |
| 5,031,634 A | 7/1991 | Simon | |
| 5,053,042 A | 10/1991 | Bidwell | |
| 5,100,387 A | 3/1992 | Ng | |
| 5,201,742 A | 4/1993 | Hasson | |
| 5,235,987 A | 8/1993 | Wolfe | |
| 5,257,975 A | 11/1993 | Foshee | |
| 5,279,564 A * | 1/1994 | Taylor | 604/104 |
| 5,312,417 A | 5/1994 | Wilk | |
| 5,316,014 A | 5/1994 | Livingston | |

(Continued)

FOREIGN PATENT DOCUMENTS

EP 577400 A1 1/1994

(Continued)

OTHER PUBLICATIONS

International Search Report for PCT/US2010/059629, dated Jul. 13, 2011.
U.S. Appl. No. 12/399,482, filed Mar. 6, 2009, Methods and Devices for Providing Access Into a Body Cavity.

(Continued)

*Primary Examiner* — Kevin T Truong
*Assistant Examiner* — Larry E Waggle, Jr.
(74) *Attorney, Agent, or Firm* — Nutter McClennen & Fish LLP

(57) ABSTRACT

Methods and devices are provided for providing surgical access into a body cavity. In general, the methods and devices allow a surgical access device to be securely positioned within an opening in tissue to provide access to a body cavity underlying the tissue. An actuator can be rotatably disposed on or in a housing of a surgical access device such that rotation of the actuator relative to the housing is effective to move a cannula of the surgical access device between an insertion configuration in which the cannula has a reduced profile enabling it to easily be inserted into a tissue opening, and an expanded profile enabling it to form an anchor against and/or within the tissue opening.

12 Claims, 11 Drawing Sheets

U.S. PATENT DOCUMENTS

| | | | |
|---|---|---|---|
| 5,320,111 A | 6/1994 | Livingston | |
| 5,330,437 A | 7/1994 | Durman | |
| 5,342,315 A | 8/1994 | Rowe et al. | |
| 5,431,676 A | 7/1995 | Dubrul et al. | |
| 5,494,039 A | 2/1996 | Onik et al. | |
| 5,569,205 A | 10/1996 | Hart et al. | |
| 5,628,732 A | 5/1997 | Antoon, Jr. et al. | |
| 5,647,373 A | 7/1997 | Paltieli et al. | |
| 5,707,359 A | 1/1998 | Bufalini | |
| 5,857,999 A | 1/1999 | Quick et al. | |
| 5,868,673 A | 2/1999 | Vesely | |
| 5,882,340 A | 3/1999 | Yoon | |
| 5,911,707 A | 6/1999 | Wolvek et al. | |
| 5,916,175 A | 6/1999 | Bauer et al. | |
| 5,941,889 A | 8/1999 | Cermak | |
| 5,954,670 A | 9/1999 | Baker | |
| 5,984,930 A | 11/1999 | Maciunas et al. | |
| 6,017,356 A | 1/2000 | Frederick et al. | |
| D422,706 S | 4/2000 | Bucholz et al. | |
| 6,048,321 A | 4/2000 | McPherson et al. | |
| 6,110,182 A | 8/2000 | Mowlai-Ashtiani | |
| 6,162,196 A | 12/2000 | Hart et al. | |
| 6,195,577 B1 | 2/2001 | Truwit et al. | |
| 6,203,499 B1 | 3/2001 | Imling | |
| 6,216,029 B1 | 4/2001 | Paltieli | |
| 6,231,565 B1 | 5/2001 | Tovey et al. | |
| 6,231,585 B1 | 5/2001 | Takahashi et al. | |
| 6,236,875 B1 | 5/2001 | Bucholz et al. | |
| 6,245,028 B1 | 6/2001 | Furst et al. | |
| 6,283,942 B1 | 9/2001 | Staehlin et al. | |
| 6,361,499 B1 | 3/2002 | Bates et al. | |
| 6,379,307 B1 | 4/2002 | Filly et al. | |
| 6,400,979 B1 | 6/2002 | Stoianovici et al. | |
| 6,443,960 B1 | 9/2002 | Brabrand et al. | |
| 6,445,943 B1 | 9/2002 | Ferre et al. | |
| 6,451,042 B1 * | 9/2002 | Bonutti | 606/190 |
| 6,468,226 B1 | 10/2002 | McIntyre, IV | |
| 6,475,152 B1 | 11/2002 | Kelly, Jr. et al. | |
| 6,490,467 B1 | 12/2002 | Bucholz et al. | |
| 6,501,981 B1 | 12/2002 | Schweikard et al. | |
| 6,529,765 B1 | 3/2003 | Franck et al. | |
| 6,535,756 B1 | 3/2003 | Simon et al. | |
| 6,539,121 B1 | 3/2003 | Haskell et al. | |
| 6,546,279 B1 | 4/2003 | Bova et al. | |
| 6,547,782 B1 | 4/2003 | Taylor | |
| 6,551,270 B1 | 4/2003 | Bimbo et al. | |
| 6,665,554 B1 | 12/2003 | Charles et al. | |
| 6,687,531 B1 | 2/2004 | Ferre et al. | |
| 6,723,106 B1 | 4/2004 | Charles et al. | |
| 6,731,966 B1 | 5/2004 | Spigelman et al. | |
| 6,752,812 B1 | 6/2004 | Truwit | |
| 6,770,027 B2 | 8/2004 | Banik et al. | |
| 6,782,288 B2 | 8/2004 | Truwit | |
| 6,783,524 B2 | 8/2004 | Anderson | |
| 6,785,572 B2 | 8/2004 | Yanof et al. | |
| 6,808,492 B2 | 10/2004 | Snyder | |
| 6,866,655 B2 * | 3/2005 | Hackett | 604/264 |
| 7,021,173 B2 | 4/2006 | Stoianovici et al. | |
| 7,056,329 B2 | 6/2006 | Kerr | |
| 7,076,106 B2 | 7/2006 | Haskell et al. | |
| 7,083,626 B2 | 8/2006 | Hart et al. | |
| 7,163,525 B2 | 1/2007 | Franer | |
| 7,371,227 B2 | 5/2008 | Zeiner | |
| 2003/0100814 A1 | 5/2003 | Kindlein | |
| 2003/0208207 A1 | 11/2003 | Layer | |
| 2003/0229338 A1 | 12/2003 | Irion et al. | |
| 2004/0082969 A1 | 4/2004 | Kerr | |
| 2004/0185453 A1 | 9/2004 | Myerson et al. | |
| 2004/0230161 A1 | 11/2004 | Zeiner | |
| 2004/0254426 A1 | 12/2004 | Wenchell | |
| 2005/0222582 A1 | 10/2005 | Wenchell | |
| 2006/0149137 A1 | 7/2006 | Pingleton et al. | |
| 2006/0161049 A1 | 7/2006 | Beane et al. | |
| 2006/0247499 A1 | 11/2006 | Butler et al. | |
| 2006/0247673 A1 * | 11/2006 | Voegele et al. | 606/191 |
| 2007/0106319 A1 | 5/2007 | Au et al. | |
| 2007/0185453 A1 | 8/2007 | Michael et al. | |
| 2007/0260121 A1 | 11/2007 | Bakos et al. | |
| 2007/0260273 A1 | 11/2007 | Cropper et al. | |
| 2008/0086080 A1 | 4/2008 | Mastri et al. | |
| 2008/0086167 A1 | 4/2008 | Mastri et al. | |
| 2008/0132946 A1 * | 6/2008 | Mueller | 606/232 |
| 2008/0249373 A1 | 10/2008 | Wenchell | |
| 2008/0255519 A1 | 10/2008 | Piskun et al. | |
| 2009/0005799 A1 | 1/2009 | Franer et al. | |
| 2009/0082731 A1 | 3/2009 | Moreno | |
| 2009/0105659 A1 | 4/2009 | Bettuchi et al. | |
| 2010/0081863 A1 | 4/2010 | Hess et al. | |
| 2010/0081864 A1 | 4/2010 | Hess et al. | |
| 2010/0081880 A1 | 4/2010 | Widenhouse et al. | |
| 2010/0081881 A1 | 4/2010 | Murray et al. | |
| 2010/0081882 A1 | 4/2010 | Hess et al. | |
| 2010/0081883 A1 | 4/2010 | Murray et al. | |
| 2010/0081995 A1 | 4/2010 | Widenhouse et al. | |
| 2010/0118830 A1 | 5/2010 | Stephenson et al. | |
| 2010/0280326 A1 * | 11/2010 | Hess et al. | 600/206 |
| 2011/0124967 A1 | 5/2011 | Morgan et al. | |
| 2011/0144442 A1 | 6/2011 | Farrell et al. | |

FOREIGN PATENT DOCUMENTS

| | | |
|---|---|---|
| WO | 9636283 A1 | 11/1996 |
| WO | 0041759 A1 | 7/2000 |
| WO | 0062689 A1 | 10/2000 |
| WO | 0108563 A2 | 2/2001 |
| WO | 2005097019 A2 | 10/2005 |
| WO | 2005097234 A2 | 10/2005 |
| WO | 2006057982 A2 | 6/2006 |
| WO | 2006117819 A1 | 11/2006 |
| WO | 2008027375 A2 | 3/2008 |

OTHER PUBLICATIONS

U.S. Appl. No. 12/399,547, filed Mar. 6, 2009, Surgical Access Devices and Methods Providing Seal Movement in Predefined Paths.

U.S. Appl. No. 12/399,625, filed Mar. 6, 2009, Methods and Devices for Providing Access Into a Body Cavity.

U.S. Appl. No. 12/420,146, filed Apr. 8, 2009, Methods and Devices for Providing Access Into a Body Cavity.

U.S. Appl. No. 12/424,213, filed Apr. 15, 2009, Cannula With Sealing Elements.

U.S. Appl. No. 12/478,862, filed Jun. 5, 2009, Flexible Cannula Devices and Methods.

U.S. Appl. No. 12/478,882, filed Jun. 5, 2009, Multi-Planar Obturator With Foldable Retractor.

U.S. Appl. No. 12/479,030, filed Jun. 5, 2009, Retractor With Integrated Wound Closure.

U.S. Appl. No. 12/479,096, filed Jun. 5, 2009, Interlocking Seal Components.

U.S. Appl. No. 12/479,293, filed Jun. 5, 2009, Methods and Devices for Providing Access Through Tissue to Surgical Site.

U.S. Appl. No. 12/479,395, filed Jun. 5, 2009, Methods and Devices for Accessing a Body Cavity Using Surgical Access Device With Modular Seal Components.

U.S. Appl. No. 12/512,542, filed Jul. 30, 2009, Methods and Devices for Providing Access Into a Body Cavity.

U.S. Appl. No. 12/512,568, filed Jun. 30, 2009, Methods and Devices for Providing Access Into a Body Cavity.

U.S. Appl. No. 12/636,184, filed Dec. 11, 2009, Methods and Devices for Providing Access Through Tissue to a Surgical Site.

U.S. Appl. No. 12/636,191, filed Dec. 11, 2009, Methods and Devices for Providing Access Through Tissue to a Surgical Site.

U.S. Appl. No. 12/636,205, filed Dec. 11, 2009, Methods and Devices for Providing Access Through Tissue to a Surgical Site.

U.S. Appl. No. 12/636,232, filed Dec. 11, 2009, Methods and Devices for Providing Access Through Tissue to a Surgical Site.

U.S. Appl. No. 12/636,020, filed Dec. 11, 2009, Inverted Conical Expandable Retractor.

U.S. Appl. No. 12/636,023, filed Dec. 11, 2009, Inverted Concical Expandable Retractor With Coil Spring.

U.S. Appl. No. 12/635,990, filed Dec. 11, 2009, Methods and Devices for Accessing a Body Cavity.

U.S. Appl. No. 12/636,174, filed Dec. 11, 2009, Methods and Devices for Providing Access Through Tissue to a Surgical Site.

* cited by examiner

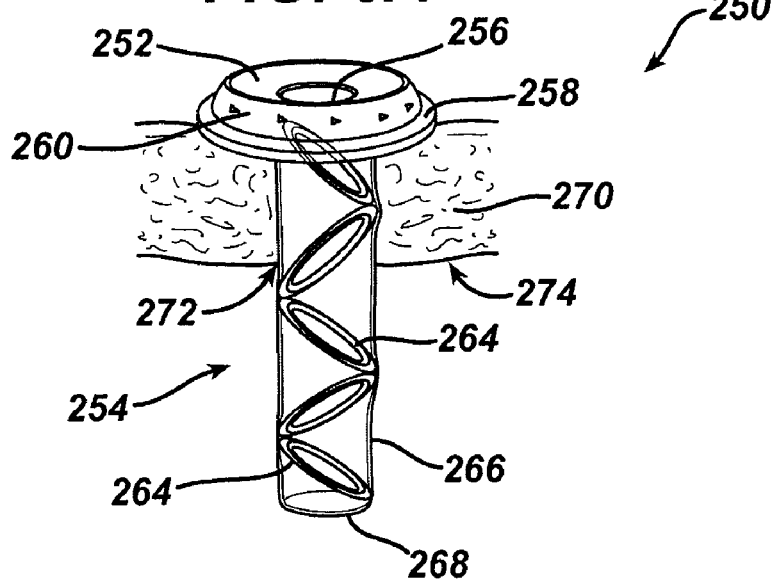
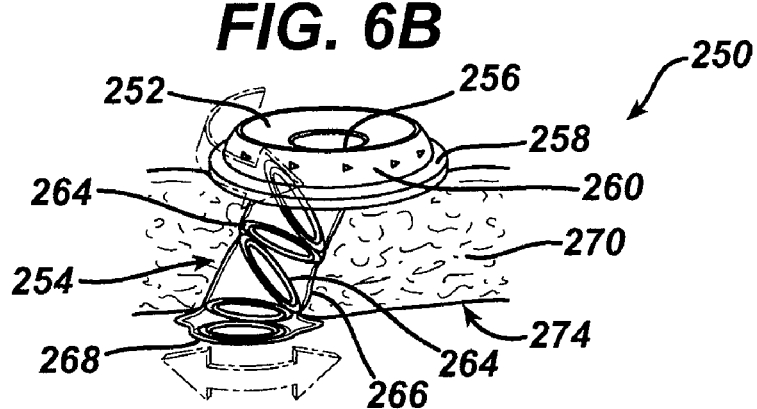
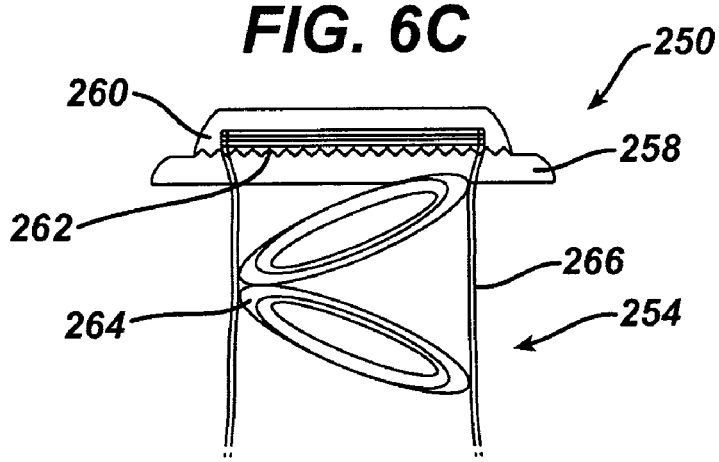

METHODS AND DEVICES FOR PROVIDING ACCESS INTO A BODY CAVITY

CROSS-REFERENCE TO RELATED APPLICATIONS

The present application is being filed with U.S. application Ser. No. 12/635,754 entitled "Methods and Devices For Providing Access Into a Body Cavity," which is incorporated by reference herein in its entirety.

FIELD OF THE INVENTION

The present invention relates to methods and devices for providing surgical access into a body cavity.

BACKGROUND OF THE INVENTION

Access ports are widely used in medical procedures to gain access to anatomical cavities ranging in size from the abdomen to small blood vessels, such as veins and arteries, epidural, pleural and subarachnoid spaces, heart ventricles, and spinal and synovial cavities. The use of access ports has become more common as they provide minimally invasive techniques for establishing a portal for a number of procedures, such as those involving the abdominal cavity. Reduced postoperative recovery time, markedly decreased post-operative pain and wound infection, and improved cosmetic outcome are well established benefits of minimally invasive surgery, derived mainly from the ability of surgeons to perform an operation utilizing smaller incisions of the body cavity wall.

In many surgical procedures, it is desirable to provide one or more working channels into a body cavity through which various instruments can be passed to view, engage, and/or treat tissue to achieve a diagnostic or therapeutic effect. In laparoscopic abdominal procedures for example, the abdominal cavity is generally insufflated with $CO_2$ gas to a pressure of around 15 mm Hg. The abdominal wall is pierced and one or more tubular cannulas, each defining a working channel, are inserted into the abdominal cavity. A laparoscopic telescope connected to an operating room monitor can be used to visualize the operative field and can be placed through one of the working channels. Other laparoscopic instruments such as graspers, dissectors, scissors, retractors, etc. can also be placed through one or more of the working channels to facilitate various manipulations by the surgeon and/or surgical assistant(s).

One problem with existing methods and devices is that existing surgical access devices do not retract tissue beyond the initial incision to any appreciable degree. It can thus be difficult to position a surgical access device in the incision, particularly in minimally invasive surgical procedures where the incision is relatively small. It can also be difficult as an initial matter to choose an appropriately sized access device to position within the incision during the stress and time constraints of surgery.

Removal of an access device from an incision in tissue can present further challenges when the access device is snugly positioned therein, requiring an amount of pullout force that can cause damage to the tissue and/or prolong length of the surgical procedure. Such forceful removal of the access device can also increase the size of the incision, thereby reducing the healing and cosmetic benefits of a minimally invasive surgical procedure.

Accordingly, there remains a need for methods and devices for providing surgical access into a body cavity.

SUMMARY OF THE INVENTION

The present invention generally provides methods and devices for providing surgical access into a body cavity. In one embodiment, an adjustable access device is provided and can include a housing having a cannula extending distally therefrom defining a working channel extending therethrough for receiving surgical instruments. The housing can have one or more ports formed therein for receiving surgical instruments, and at least one seal can be disposed in the working channel and can be configured to form at least one of a seal around an instrument disposed through the working channel and a seal across the working channel when no instrument is disposed through the working channel. The surgical access device can also include an actuator rotatably disposed on the housing such that rotation of the actuator relative to the housing is effective to move the cannula between an insertion configuration in which the cannula has a first outer diameter and a first length, and a deployed configuration in which the cannula has a second outer diameter and a second length. In an exemplary embodiment, the first outer diameter can be less than the first length of the cannula and the second outer diameter can be greater than the first outer diameter and the second length being less than the first length. The second outer diameter can be less than the second length of the cannula.

While the cannula can have many configurations, in one exemplary embodiment, the cannula can include a flexible band formed into a helix having a plurality of coils. Adjacent coils can be mated together using any mechanism known in the art, for example, they can be mated to one another by a mating feature formed on the coils. The mating feature can include one of a male track and a female track formed on a first edge of each coil, and one of a complementary male track or female track formed on a second opposite edge of each coil.

In other exemplary embodiments, a proximal portion of the flexible band can be mated to the actuator. Rotation of the actuator to move the cannula to the insertion configuration can be effective to wind the proximal portion of the flexible band around the actuator to cause the cannula to increase in length and decrease in diameter to facilitate insertion of the cannula into and removal of the cannula from a tissue opening. Rotation of the actuator to the deployed configuration can be effective to unwind the proximal portion of the flexible band from around the actuator to cause the cannula to decrease in length and increase in diameter. In one embodiment, the cannula can be configured to engage a tissue opening in the deployed configuration to thereby stabilize the access device.

In other aspects, an adjustable access device is provided and can include a housing having an adjustable cannula extending therefrom. The housing and the cannula can define a working channel therethrough. The adjustable cannula can include a flexible band wound into a helical spring such that a proximal end of the flexible band is coupled to the housing and a distal end of the band is positioned at a distal end of the adjustable cannula. In some embodiments, the adjustable cannula can have an insertion configuration with an increased length and decreased diameter for insertion into a tissue opening and a deployed configuration with a decreased length and increased diameter for anchoring within a tissue opening.

The housing can include an actuator coupled to the proximal end of the flexible band and configured to rotate the proximal end of the flexible band to move the cannula between the insertion and deployed configurations. The adjustable cannula can have a substantially constant first diameter in the insertion configuration and a substantially constant second diameter in the deployed configuration. In some embodiments, the flexible band can be formed into a helix having a plurality of coils coupled together.

Exemplary methods are also provided and in one embodiment, a method of providing access through tissue to a body cavity is provided and can include positioning a cannula in an opening in tissue such that a working channel of the cannula provides access through the tissue and into a body cavity. The method can also include rotating an actuator to move the cannula from an insertion configuration to a deployed configuration in which the cannula decreases in length and increases in diameter, and rotating the actuator to move the cannula to the insertion configuration in which the cannula increases in length and decreases in diameter to increase a size of the opening in the tissue. The method can further include removing the cannula from the opening in tissue. In some embodiments, rotating the actuator to move the cannula to the deployed configuration can anchor the cannula against the tissue through which it extends.

Rotating the actuator to move the cannula to the insertion configuration can wind a proximal end of a flexible band around the actuator to tighten a helix formed by the flexible band. Furthermore, rotating the actuator to move the cannula to the deployed configuration can unwind a proximal end of a flexible band from around the actuator to loosen a helix formed by the flexible band.

In other aspects, an adjustable access device is provided and can include a housing having an adjustable cannula extending distally therefrom. The adjustable cannula can be movable between an insertion configuration and a deployed configuration in which a distal portion of the cannula inverts radially outward relative to a proximal portion of the cannula to form an anchor configured for stabilizing the access device. The anchor can have a diameter greater than a diameter of the proximal portion of the cannula. In some embodiments, the cannula can be configured to telescope within the housing in the insertion configuration.

The adjustable access device can also include a rotatable actuator disposed on the housing and configured to move the cannula between the insertion configuration and the deployed configuration. The cannula can be formed from many materials, for example, the cannula can be formed of a plurality of fibers woven into a mesh material. The rotatable actuator can be configured to decrease a length of at least some of the plurality of fibers extending from the housing to move the cannula to the deployed configuration.

In other embodiments, an adjustable access device is provided that can include a housing and a cannula formed of a weave of fibers extending distally from the housing. The housing and the cannula can define a working channel extending therethrough for receiving instruments. In one exemplary embodiment, an actuator can be rotatably disposed on the housing such that rotation of the actuator in a first direction relative to the housing is effective to cause a distal portion of the cannula to invert radially outward into a deployed configuration to form a distal anchor to engage tissue. The distal anchor can include a distal rim configured to engage tissue when the distal anchor is in the deployed configuration.

In some embodiments, a first group of fibers from the weave of fibers can be coupled to the actuator, and a second group of fibers from the weave of fibers can not be coupled to the actuator. Rotation of the actuator in the first direction can be effective to shorten a length of the first group of fibers, and the second group of fibers can be configured to maintain an original length when the actuator is rotated in the first direction. The actuator can be rotatable in a second opposite direction to move the anchor portion of the cannula from the deployed configuration to an insertion configuration in which the cannula has a substantially constant outer diameter.

The housing can have many configurations and can include any number of sealing ports formed therein. In some embodiments, the cannula can be configured to telescope longitudinally through the housing when the actuator is rotated in the first direction. The anchor portion can have any diameter as needed, for example, the anchor portion can have a diameter substantially greater than a diameter of the cannula when in the deployed configuration. The device can further include at least one sealing element disposed within the working channel that can be effective to form at least one of a seal around an instrument inserted through the working channel and a seal across the working channel when no instrument is inserted through the working channel.

A method of providing access through tissue to a body cavity is also provided and can include positioning a cannula of a surgical access device into an opening within tissue, and rotating an actuator of the surgical access device to move the cannula from an insertion configuration to a deployed configuration in which a distal portion of the cannula inverts radially outward relative to a proximal portion of the cannula to form an anchor against the tissue.

The cannula can be formed of any material, but in one embodiment, the cannula is formed of a plurality of fibers woven into a mesh material and rotating the actuator to move the cannula to the deployed configuration rotates a first group of the plurality of fibers to shorten the fibers relative to a second group of the plurality of fibers to invert the cannula. In addition, rotating the actuator to move a cannula longitudinally through the housing can telescope the cannula longitudinally through the housing.

BRIEF DESCRIPTION OF THE DRAWINGS

The invention will be more fully understood from the following detailed description taken in conjunction with the accompanying drawings, in which:

FIG. 5C is a top view of multiple wire embodiments usable with the device of FIG. 5A;

FIG. 6A is a partial cross-sectional view of another embodiment of an adjustable surgical access device having a flexible cannula with multiple stability rings shown in an insertion configuration;

FIG. 6B is a partial cross-sectional view of the device of FIG. 6A showing the cannula in a deployed configuration;

FIG. 6C is a cross-sectional view of the device of FIG. 6A showing an actuator;

DETAILED DESCRIPTION OF THE INVENTION

Figure 1A:
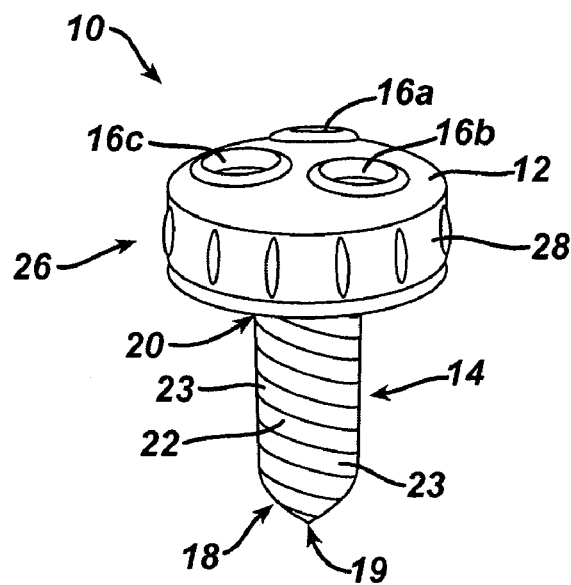
FIG. 1A is a perspective view of one embodiment of an adjustable surgical access device having a helical cannula shown in a deployed configuration.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Various exemplary methods and devices are provided for surgically accessing a body cavity. In general, the methods and devices allow a surgical access device to be securely positioned within an opening in tissue to provide access to a body cavity underlying the tissue. In one embodiment, an adjustable access device is provided and can include a housing having a cannula extending distally therefrom. The housing and the cannula can define a working channel extending therethrough for receiving surgical instruments. The adjustable access device can further include at least one seal disposed within the working channel and configured to form at least one of a seal around an instrument disposed through the working channel and a seal when no instrument is disposed through the working channel. An actuator can be rotatably disposed on or in the housing such that rotation of the actuator relative to the housing is effective to move the cannula between an insertion configuration in which the cannula has a reduced profile enabling it to easily be inserted into a tissue opening, and an expanded configuration enabling the cannula to form an anchor against and/or within the tissue opening.

The adjustable access device can allow for ease of insertion into an opening in tissue. An exemplary cannula of the surgical access device can have a reduced profile in an insertion configuration so that it can be inserted into a smaller tissue opening. A smaller tissue opening can improve recovery time and cosmetic outcome of a procedure. Once positioned within the tissue opening, the cannula of the adjustable access device can be moved to a deployed configuration that can provide active retraction of the tissue opening to help anchor the device within the tissue. Such anchoring can help form a better seal between the tissue and the device and help retain the device in a more stable position within the tissue. Once a procedure is complete, the cannula of the surgical access device can be returned to its reduced profile insertion configuration to enable easy removal from the tissue opening.

The various surgical access devices described herein can generally be configured to allow one or more surgical instruments to be inserted through one or more independent sealing ports or access ports formed in a housing of the device and into a body cavity. The sealing ports can each define working channels extending through the housing and in communication with a cannula extending distally from the housing. The cannula can be configured as a wound protector, retractor, or other member for forming a pathway through tissue. The cannula can generally be configured to be positioned within any opening in a patient's body, including a natural opening or an incision. The elasticity of the skin of the patient can assist in the retention of the cannula in the body opening or incision made in the body. In one embodiment, the cannula can be substantially flexible so that it can be easily maneuvered into and within tissue as needed. In other embodiments, the cannula can be substantially rigid or substantially semi-rigid and adjustable or expandable in shape/size. The cannula can be formed of any suitable material known in the art, e.g., silicone, urethane, thermoplastic elastomer, and rubber.

Any and all of the surgical access devices described herein can also include various other features, such as one or more ventilation ports to allow evacuation of smoke during procedures that utilize cautery, and/or one or more insufflation ports through which the surgeon can insufflate the abdomen to cause pneumoperitenium, as described by way of non-limiting example in U.S. Patent Application No. 2006/0247673 entitled "Multi-port Laparoscopic Access Device" filed Nov. 2, 2006, which is hereby incorporated by reference in its entirety. The insufflation port can be located anywhere on the device, can have any size, and can accept a leur lock or a needle, as will be appreciated by those skilled in the art.

Any and all embodiments of a surgical access device can also include one or more safety shields positioned through, in, and around any of the components and/or tissue to protect the components against puncture or tear by surgical instruments being inserted through the device. Exemplary embodiments of safety shields are described in more detail in U.S. Patent Publication No. 2006/0247673 entitled "Multi-port Laparoscopic Access Device" filed Nov. 2, 2006, U.S. patent application Ser. No. 12/399,625 entitled "Methods and Devices for Providing Access to a Body Cavity" filed on Mar. 6, 2009, U.S. patent application Ser. No. 12/399,482 entitled "Methods and Devices for Providing Access to a Body Cavity" filed on Mar. 6, 2009, and U.S. patent application Ser. No. 12/242,765 entitled "Surgical Access Device" filed on Sep. 30, 2008, which are hereby incorporated by reference in their entireties.

In any and all of the surgical access device embodiments disclosed herein, an engagement and/or release mechanism can be included to allow certain components of the surgical access device to be removable as needed. Any engagement and release mechanism known in the art, e.g., a snap-lock mechanism, corresponding threads, etc., can be used to releasably mate components of the device. Exemplary embodiments of engagement and release mechanisms are described in more detail in previously mentioned U.S. patent application Ser. No. 12/242,765 entitled "Surgical Access Device" filed on Sep. 30, 2008, U.S. patent application Ser. No. 12/399,625 entitled "Methods and Devices for Providing Access to a Body Cavity" filed on Mar. 6, 2009, and U.S. patent application Ser. No. 12/399,482 entitled "Methods and Devices for Providing Access to a Body Cavity" filed on Mar. 6, 2009 and in U.S. Pat. No. 7,371,227 entitled "Trocar Seal Assembly," issued May 13, 2008 and U.S. Pat. No. 5,628,732 entitled "Trocar With Improved Universal Seal," issued May 13, 2007, which are hereby incorporated by reference in their entireties.

Typically, during surgical procedures in a body cavity, such as the abdomen, insufflation is provided through the surgical access device to expand the body cavity to facilitate the surgical procedure. Thus, in order to maintain insufflation within the body cavity, most surgical access devices include at least one seal disposed therein to prevent air and/or gas from escaping when surgical instruments are inserted therethrough. Various sealing elements are known in the art, but typically the surgical access device can include at least one instrument seal that forms a seal around an instrument disposed therethrough, but otherwise does not form a seal when no instrument is disposed therethrough; at least one channel seal or zero-closure seal that seals the working channel created by the sealing port when no instrument is disposed therethrough; or a combination instrument seal and channel seal that is effective to both form a seal around an instrument disposed therethrough and to form a seal in the working channel when no instrument is disposed therethrough. A person skilled in the art will appreciate that various seals known in the art can be used including, e.g., duckbill seals, cone seals, flapper valves, gel seals, diaphragm seals, lip seals, iris seals, etc. A person skilled in the art will also appreciate that any combination of seals can be included in any of the embodiments described herein, whether or not the seal combinations are specifically discussed in the corresponding description of a particular embodiment. Exemplary embodiments of various seal protectors are described in more detail in U.S. Pat. No. 5,342,315 entitled "Trocar Seal/Protector Assemblies," issued Aug. 30, 1994 and U.S. Pat. No. 7,163,525 entitled "Duckbill Seal Protector," issued Jan. 16, 2007, which are hereby incorporated by reference in their entireties.

Figure 1B:
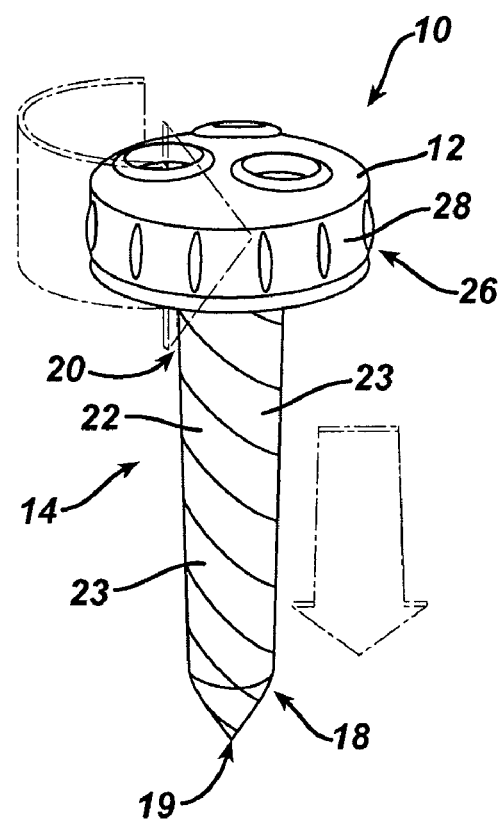
FIG. 1B is a perspective view of the device of FIG. 1A showing the cannula in an insertion configuration.

FIGS. 1A and 1B illustrate one embodiment of a surgical access device 10 having a housing 12 configured to have one or more surgical instruments inserted therethrough. The housing 12 can be fixedly or removably coupled to a cannula 14 that extends distally from the housing 12 to provide a pathway through tissue into a body cavity. The housing 12 can be in a fixed position relative to the cannula 14 as shown in this embodiment, or the housing 12 can be movable relative to the cannula 14. Exemplary embodiments of various housings are described in more detail in previously mentioned U.S. Patent Publication No. 2006/0247673 entitled "Multi-port Laparoscopic Access Device" filed Nov. 2, 2006, U.S. patent application Ser. No. 12/399,625 entitled "Methods and Devices for Providing Access to a Body Cavity" filed on Mar. 6, 2009, U.S. patent application Ser. No. 12/399,482 entitled "Methods and Devices for Providing Access to a Body Cavity" filed on Mar. 6, 2009, and U.S. patent application Ser. No. 12/242,765 entitled "Surgical Access Device" filed on Sep. 30, 2008, and in U.S. patent application Ser. No. 12/399,547 entitled "Surgical Access Devices And Methods Providing Seal Movement In Predefined Paths" filed on Mar. 6, 2009, which is hereby incorporated by reference in its entirety.

While any number of sealing ports can be formed in the housing 12, in the illustrated embodiment, three sealing ports 16a, 16b, 16c extend through the housing 12. The sealing ports 16a, 16b 16c each have a central axis that extends substantially parallel with a central longitudinal axis of the housing 12, but any one or more of the sealing ports 16a, 16b, 16c can be angled relative to the housing 12 and/or rotatable or otherwise movable relative to the housing 12. Additionally or alternatively, any one or more of the sealing ports 16a, 16b, 16c can be configured to be movable relative to any one or more portions of the cannula 14 and/or any others of the sealing ports 16a, 16b, 16c. Each sealing port, or any other portion of the housing or cannula, can include one or more sealing elements. A sealing element can include an instrument seal, a channel seal, and/or a combination instrument/channel seal as previously discussed herein. As will be appreciated by those skilled in the art, any configuration and any number of sealing ports can be used in any of the housing and cannula embodiments disclosed herein. Exemplary embodiments of various sealing ports are described in more detail in previously mentioned U.S. Patent Publication No. 2006/0247673 entitled "Multi-port Laparoscopic Access Device" filed Nov. 2, 2006, U.S. patent application Ser. No. 12/399, 625 entitled "Methods and Devices for Providing Access to a Body Cavity" filed on Mar. 6, 2009, U.S. patent application Ser. No. 12/399,482 entitled "Methods and Devices for Providing Access to a Body Cavity" filed on Mar. 6, 2009, and U.S. patent application Ser. No. 12/242,765 entitled "Surgical Access Device" filed on Sep. 30, 2008.

Figure 1C:
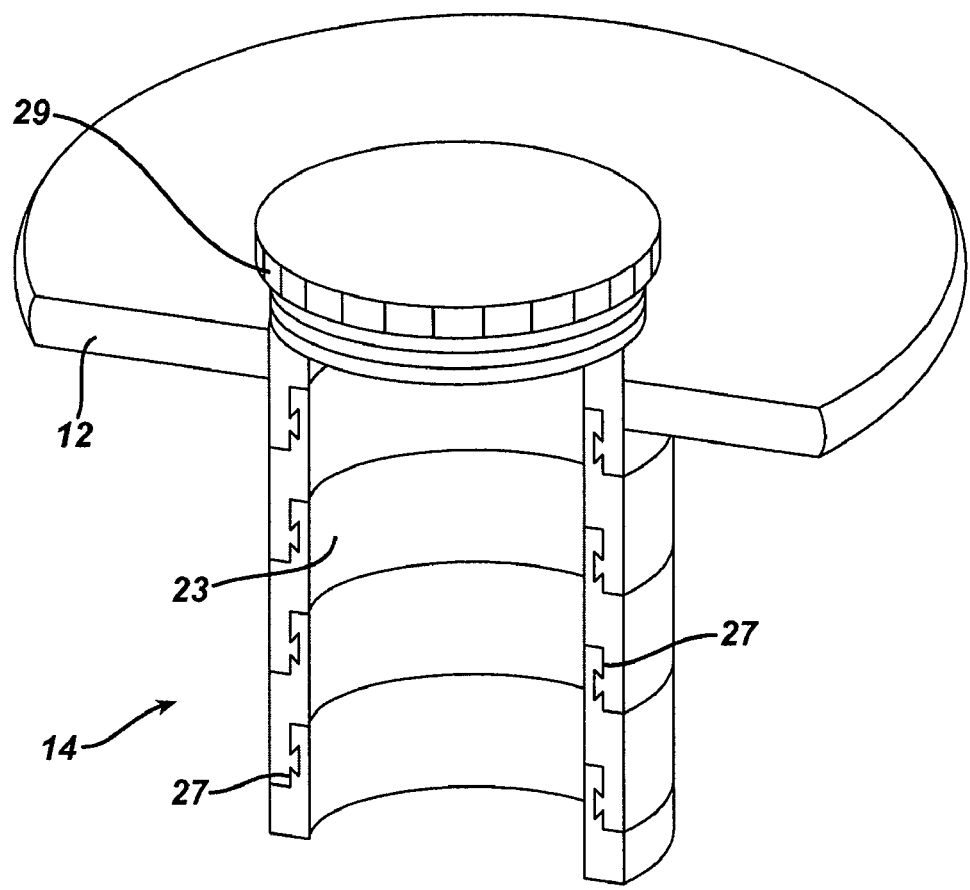
FIG. 1C is a perspective cross-sectional view of the cannula of the device of FIG. 1A

While the cannula 14 can have any configuration known in the art, in the illustrated embodiment, the cannula 14 is in the shape of a cylindrical elongate member having a proximal end 20 and a substantially constant outer diameter that terminates in a conical distal tip 18, however the distal end 18 can have any configuration, including cylindrical. The distal end 18 can have an opening 19 formed therein for receiving an obturator or other tissue penetrating tool, as well as surgical instruments inserted through the device 10. In an exemplary embodiment, a length of the cannula 14 is generally greater than a diameter of the cannula 14, although it will be appreciated that in some embodiments, the diameter of the cannula 14 could possibly be greater than its length. In this particular embodiment, the cannula 14 can be formed of an elastic and/or flexible band 22 that is wound into the shape of a helix, spring, and/or spiral. Helical coils 23 of the flexible band 22 can define a lumen of the cannula 14. The helical coils 23 can each be mated to adjacent coils 23 such that there is no space between the coils 23, or alternatively, a sheath or other connecting element can be disposed within and/or around the coils 23 to mate the coils 23 and prevent fluid flow therebetween. While any mating mechanism known in the art can be used to mate adjacent coils 23, in the illustrated embodiment, each coil 23 can have one of a male and female rail and/or track formed on each proximal and distal end that is configured to mate with a corresponding male or female track on an adjacent coil 23. In this way, the coils 23 can interlock together. For example, as illustrated in FIG. 1C, each coil can have interlocking end portions 27 similar to a zip lock connection that secures the coils together.

A proximal-most end of the flexible band 22 of the cannula 14 can be coupled to an actuator 26 positioned within the housing 12. The actuator 26 can take any form known in the art, but in one exemplary embodiment, the actuator 26 can have an external portion 28 that can be gripped by a user to facilitate rotation. The actuator 26 can further include an internal circular wheel 29 that is coupled to the external portion 28 and that can be rotated in either direction relative to the housing 12 and relative to the cannula 14 via the external portion 28. The proximal-most end of the flexible band 22 can be attached to and/or wound around the circular wheel such that rotation of the actuator 26 in a first direction is effective to wind the flexible band 22 around the circular wheel. In addition, rotation of the actuator 26 in a second opposite direction is effective to unwind the flexible band 22 from around the circular wheel. The first and second directions are generally opposite directions and can be either clockwise or counter-clockwise as needed. In the illustrated embodiment, the first direction is clockwise and the second direction is counter-clockwise.

Rotation of the actuator 26 in the first direction can wind the flexible band 22 around the circular wheel, thereby tightening the helical cannula 14 into an insertion configuration. Because the coils 23 are interlocked together as described above, tightening of the flexible band 22 causes the helical cannula 14 to decrease in diameter and thus increase in length to facilitate easier insertion of the cannula 14 into a tissue opening. Rotation of the actuator 26 in the second direction can unwind the flexible band 22 from around the circular wheel, thereby causing the helical cannula 14 to increase in diameter and decrease in length into an anchoring and/or deployed configuration. The deployed configuration can cause the cannula 14 to press against the tissue and can allow the cannula 14 to act as an anchor against tissue within the opening to stabilize the access device 10. In some embodiments, the cannula 14 can act as a distal anchor within the tissue and the housing 12 can act as a proximal anchor on the surface of the tissue to stabilize the device 10 on both sides of the tissue. Due to the nature of the flexible band 22 having an expanded diameter in the deployed configuration, a biasing spring force can be created between the cannula 14 and the housing 12, thereby providing stabilization for the device.

In some embodiments, the cannula 14 can be biased to the deployed configuration and/or to the insertion configuration. In other embodiments, the device 10 can include a latch mechanism or other locking feature to lock the cannula 14 in either of the deployed and insertion configurations. The cannula 14 can also be formed of a material that can cause the cannula 14 to be biased to one or other of the deployed and insertion configurations and/or to return to the deployed or insertion configuration under specific conditions.

In use, the actuator 26 of the surgical access device 10 can be rotated in the first direction to move the cannula 14 to the insertion configuration in which the cannula 14 increases in length and decreases in diameter. The cannula 14 can then be inserted into an opening in a patient through which a surgical procedure is to be performed. Once inserted, the actuator 26 can be rotated in the second direction to cause the cannula 14 to decrease in length and increase in diameter. The cannula 14 can increase in diameter until it contacts and applies nominal pressure against sidewalls of the tissue opening. In this way, the cannula 14 can act as both an anchor within the tissue opening and a working channel through the tissue opening through which a procedure can be performed. Once the procedure is complete, the actuator 26 can once again be rotated in the first direction to wind the flexible band 22 around the circular wheel of the actuator 26. The decreasing diameter of the cannula 14 causes the cannula 14 to disengage from the tissue opening. The surgical access device 10 can then be removed from the tissue opening.

Figure 2A:
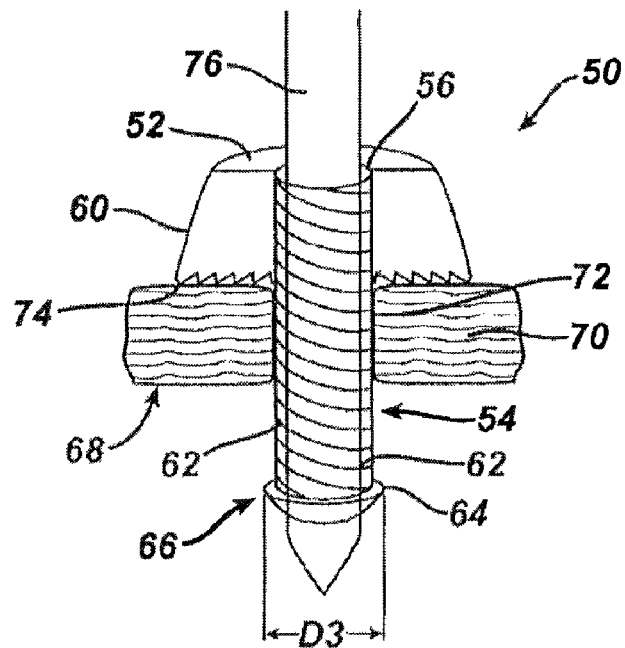
FIG. 2A is a cross-sectional view of another embodiment of an adjustable surgical access device having an invertible anchor shown in an insertion configuration.
Figure 2B:
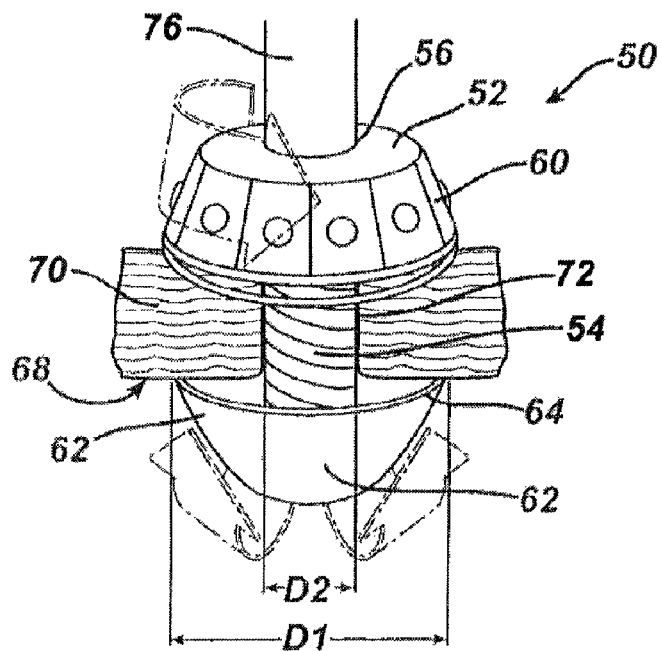
FIG. 2B is a perspective view of the device of FIG. 2A showing the anchor in a deployed configuration.

In another embodiment illustrated in FIGS. 2A and 2B, an adjustable surgical access device 50 is provided having a housing 52 with a cannula 54 extending therefrom. An insertion configuration of the surgical access device 50 is shown in FIG. 2A, and a deployed configuration is shown in FIG. 2B.

The housing 52 of the surgical access device 50 can include any number of sealing ports as needed, for example, two, three, four, etc., but in the illustrated embodiment, the housing has a single sealing port 56 extending therethrough with a central longitudinal axis aligned with a central longitudinal axis of the surgical access device 50. The cannula 54 can have many configurations, but in the illustrated embodiment, the cannula 54 is formed from a plurality of flexible fibers 62 woven into a mesh material. The individual fibers 62 can be formed from any material, including, but not limited to polypropylene, polyethylene, nylon and/or liquid crystal polymer. These fibers 62 can be woven into a mesh material and, in some embodiments, can be disposed within and/or around a flexible sheath or other protective covering to prevent instruments from snagging on the mesh when they are inserted through the cannula 54.

The cannula 54 can be moved between the insertion configuration and the deployed configuration. As shown in the insertion configuration in FIG. 2A, the cannula 54 can be elongate and can have a distal rim 64 that is inverted radially outward from the cannula 54. In other embodiments, the cannula 54 can be an elongate cylinder without an inverted distal rim 64 in the insertion configuration. In some embodiments, the cannula 54 can initially be telescoped within the housing 52 in the insertion configuration. As a tissue puncturing element, for example, an obturator, is inserted through the housing 52 to facilitate insertion of the device 50 into tissue, the cannula 54 can be telescoped out of the housing 52 by the obturator and into its elongate form shown in FIG. 2A. In the deployed configuration, the cannula 54 can be retroflexed radially outward, as shown in FIG. 2B, such that the retroflexed distal portion of the cannula 54 has a diameter D1 substantially greater than the a diameter D2 of the proximal portion of the cannula 54, and greater than a maximum diameter D3 of the distal rim 64 in the insertion configuration.

A proximal end of the cannula 54 can be coupled to an actuator 60 disposed on the housing 52. Rotation of the actuator 60 can be effective to move the cannula 54 between the insertion and deployed configurations. For example, since the distal end 66 of the cannula 54 is flipped radially outward, rotation of the actuator 60 in a first direction can cause the cannula 54 to continue to retroflex outward and upward as it moves to the deployed configuration. As noted above, the cannula 54 can be formed from a plurality of fibers 62. Shortening some fibers 62 while leaving other fibers 62 loose at their original length can cause the cannula 54 to roll outward at the distal end. Thus, a first group of fibers 62 can be attached to the actuator 60, while a second group of fibers 62 are not. For example, every third, fourth, fifth, etc. fiber 62 in the mesh material can be attached to the actuator 60 such that when the actuator 60 is rotated in the first direction, only those fibers 62 that are attached to the actuator 60 will rotate with the actuator 60 and thereby be tightened and shortened. The shortening of the first group of fibers 62 while the second group of fibers 62 remain their original length will cause the cannula 54 to retroflex radially outward and upward (i.e., proximally). Rotation of the actuator 60 in a second direction can lengthen the first group of fibers 62 coupled to the actuator 60 and thereby cause the cannula 54 to relax back to its elongate shape in the insertion configuration. As will be appreciated by those skilled in the art, the first and second directions can generally be in opposite directions and can each be clockwise or counter-clockwise as needed. In the illustrated embodiment, the first direction is in the counter-clockwise direction as shown in FIG. 2A, and the second direction is in the clockwise direction.

When the actuator 60 is rotated to cause the cannula 54 to retroflex radially outward and upward, the distal rim 64 of the cannula 54 can act as an anchor against an inner surface 68 of tissue 70 to assist in stabilizing the access device 50. The actuator 60 can have a tightening assembly, for example, a ratchet style slip-clutch tightening assembly 74, that prevents the cannula 54 from overstressing the inner surface 68 of the tissue 70 as the cannula is inverted. The slip clutch assembly 74 can have detents that resist inadvertent dilation or uncoiling of the mechanism. The detents act as a resting location to hold the housing head in its desired rotation, and due to a mechanical disadvantage, forces on the cannula cannot reverse the actuator 60. Once the distal rim 64 of the cannula 54 encounters resistance from the tissue 70, the slip-clutch or other protection mechanism prevents further tightening of the first group of fibers 62, and thereby prevents the distal rim 64 of the cannula 54 from pressing harder against the tissue 70. In this way, the distal end 66 of the cannula 54 can act as an anchor to stabilize the device. In some embodiments, the housing 52 can act as a proximal anchor while the distal end of the cannula 54 acts a distal anchor to further stabilize the device 50.

In use, the surgical access device 50 can be inserted into a tissue opening 72 using, for example, an obturator 76. Once the cannula 54 is in position within the opening 72, the actuator 60 can be rotated in the first direction to cause the cannula 54 to retroflex radially outward and upward into engagement with the inner surface 68 of the tissue 70. In this way, the cannula 54 acts as both an anchor within the tissue opening 72 and a working channel through the tissue opening 72 through which a procedure can be performed. Once the procedure is complete, the actuator 60 can be rotated in the second direction to release the first group of fibers 62 of the cannula 54, allowing the cannula 54 to return to its elongate configuration. The surgical access device 50 can then be removed from the tissue opening 72.

Figure 3A:
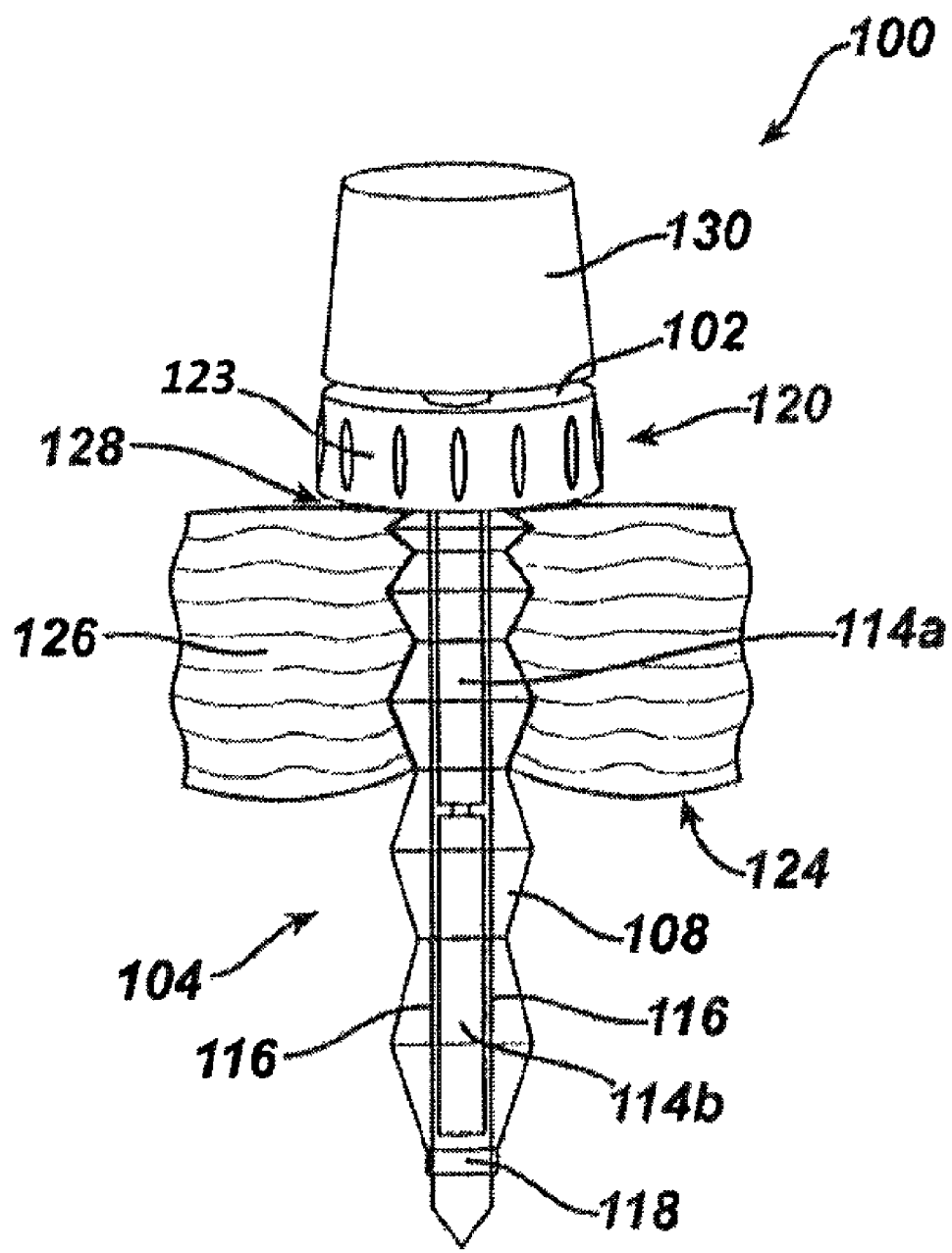
FIG. 3A is a partial cross-sectional view of one embodiment of an adjustable surgical access device having a cannula in the form of a retractable bellows shown in an insertion configuration.
Figure 3B:
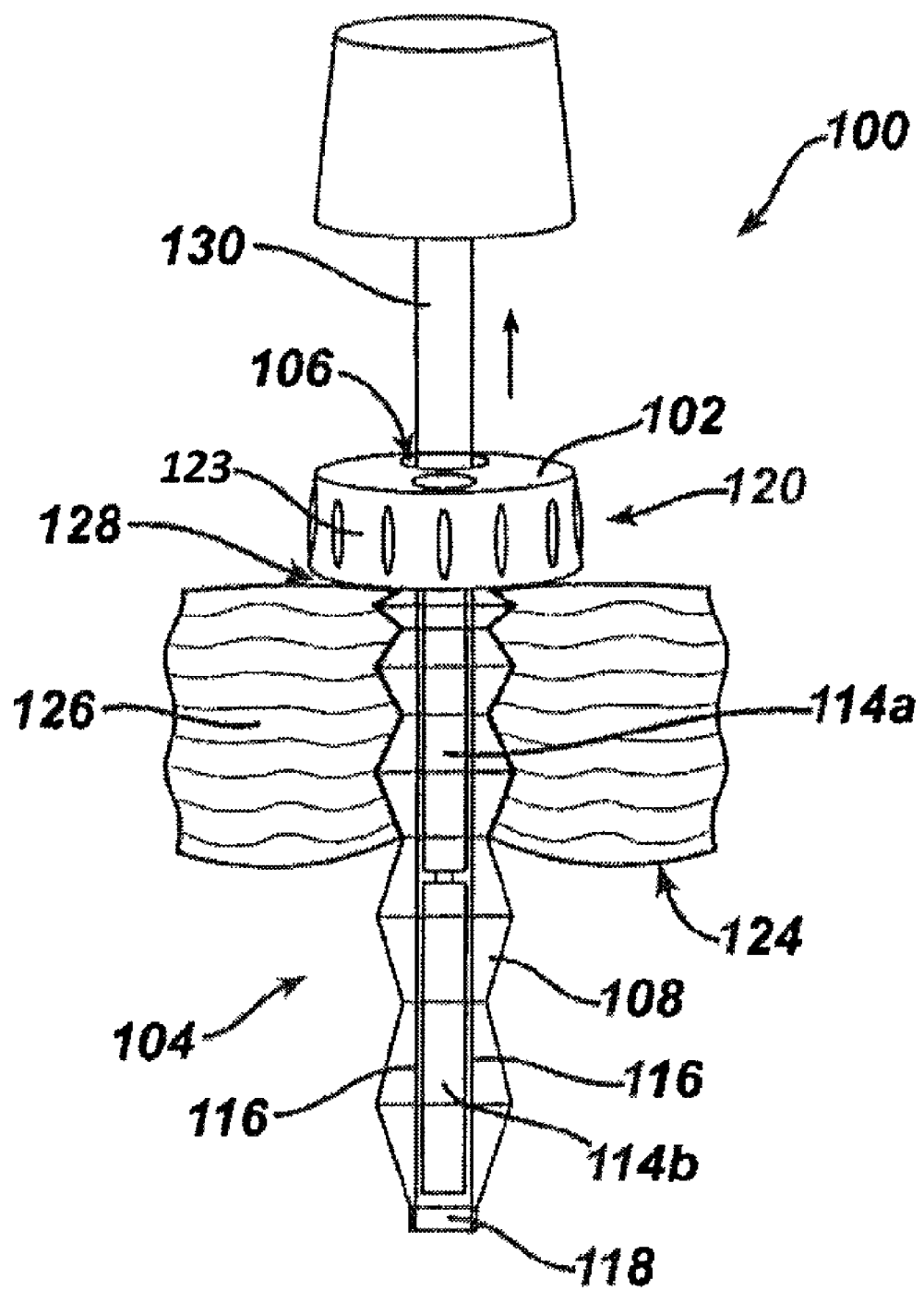
FIG. 3B is a partial cross-sectional view of the device of FIG. 3A showing an obturator being removed.
Figure 3C:
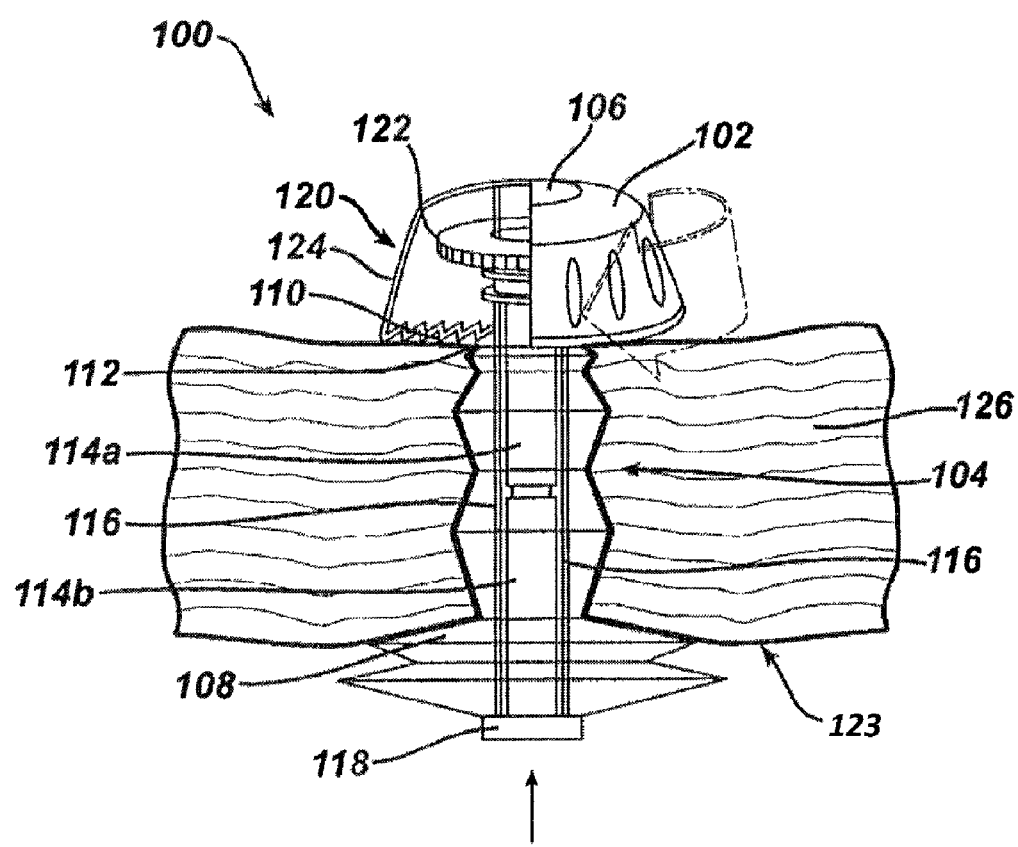
FIG. 3C is a partial cross-sectional view of the device of FIG. 3A showing the cannula in a deployed configuration.

In a further embodiment illustrated in FIGS. 3A-3C, a surgical access device 100 is provided having a housing 102 with a cannula 104 extending therefrom. The housing 102 can include any number of sealing ports as needed, for example, two, three, four, etc., but in the illustrated embodiment, the housing 102 can include a single sealing port 106 extending therethrough with a central longitudinal axis aligned with a central longitudinal axis of the surgical access device 100. As shown, the cannula 104 can include retractable bellows 108 that can be expanded and retracted as need for insertion and anchoring. The bellows 108 can have foldable walls that can fold together in response to retraction. The folds in the bellows 108 can be equally spaced and/or can be spaced further apart at a distal end of the bellows 108. A proximal end of the cannula 104 can have a radial lip 110, shown in FIG. 3C, that can slidably mate with a distal end 112 of the housing 102 such that the housing 102 can be rotated relative to the cannula 104 without causing rotation of the cannula 104. Any mating technique known in the art can be used, but in one exemplary embodiment, there can be a slidable interference fit between the radial lip 110 and the distal end 112 of the housing 102.

The cannula 104 can also include a set of telescoping inner tubes 114a, 114b disposed inside the retractable bellows 108. The telescoping inner tubes 114a, 114b can be arranged vertically inside the retractable bellows 108, one on top of the other, such that a distal tube 114b moves inside a proximal tube 114a when the bellows 108 are retracted in a proximal direction toward the housing. The tubes 114a, 114b can be joined by, for example, a sliding joint or they can be threaded together at a distal end of the proximal tube 114a and a proximal end of the distal tube 114b. The set of telescoping tubes 114a, 114b can provide a smooth cylindrical working channel through the cannula 104 for surgical instruments even when the bellows 108 are retracted, as shown in FIG. 3C.

One or more tension cables, preferably two tension cables 116, can extend proximally from opposed sides of a distal end ring 118 of the cannula 104 to an actuator 120 disposed within the housing 102. In one exemplary embodiment, the cables 116 can be positioned between the bellows 108 and the inner telescoping tubes 114a, 114b, although they can also be positioned outside of the bellows 108 or inside of the telescoping tubes 114a, 114b. A proximal end of the cables 116 can be coupled to a circular wheel 122 of the actuator 120 such that rotation of an external portion 123 of the actuator 120 in a first direction can wind the cables 116 around the circular wheel 122. This can cause a length of the cables 116 to shorten, thereby drawing the distal end ring 118 proximally. This can force the bellows 108 to collapse and the telescoping tubes 114a, 114b to telescope proximally. A proximal portion of the bellows 108 that is disposed within tissue 126 can collapse more easily than the bellows portion outside of the tissue and thus can be caused to expand outward into engagement with a tissue opening 128. A distal portion of the bellows 108 not disposed within the tissue 126 can be pulled against an inner surface 124 of the tissue 122 and can anchor against the tissue 126 to help stabilize the access device 100. Rotation of the actuator 120 in a second direction can unwind the cables 116 from the circular wheel 122 of the actuator 120, thereby lengthening the cables 116 and causing the bellows 108 to unfold from their collapsed configuration. As will be appreciated by those skilled in the art, the first and second directions can generally be in opposite directions and can each be clockwise or counter-clockwise as needed. In the illustrated embodiment, the first direction is in the clockwise direction as shown in FIG. 3C, and the second direction is in the counter-clockwise direction.

In use, the surgical access device 100 can be inserted into the opening 128 in a patient, e.g., using an obturator 130, as shown in FIGS. 3A and 3B. The retractable bellows 108 can be in an extended reduced diameter configuration during insertion. After the obturator 130 is withdrawn, the actuator 120 can be rotated in the first direction to wind the tension cables 116 around the circular wheel 122. Rotation of the actuator 120 is effective to pull the distal end ring 118 of the bellows 108 proximally, causing the bellows 108 to collapse and retract against the tissue surface 124, thereby expanding the size of the opening through the tissue. The distal telescoping tube 114b can retract inside the proximal telescoping tube 114a providing a smooth working channel through which a surgical procedure can be performed. The retracted bellows 108 can engage an inner surface of the tissue and can act as an anchor against the tissue to stabilize the access device 100. Once the surgical procedure is complete, the actuator 120 can be rotated in the second direction to unwind the tension cables 116. This causes the tension cables 116 to lengthen, thereby releasing the retractable bellows 108 back to an insertion configuration so that the surgical access device 100 can be removed from the tissue opening 128.

Figure 4A:
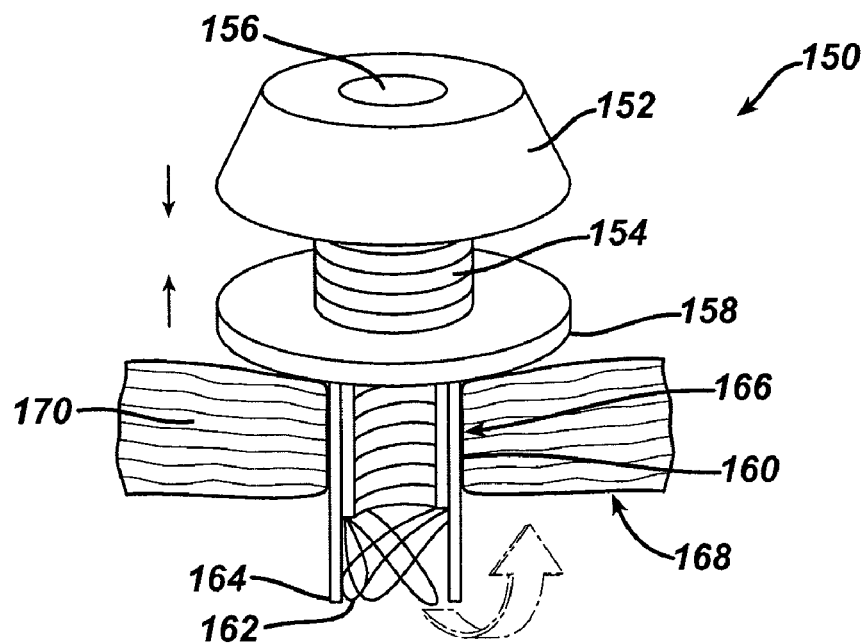
FIG. 4A is a partial cross-sectional view of another embodiment of an adjustable surgical access device shown in an insertion configuration.
Figure 4B:
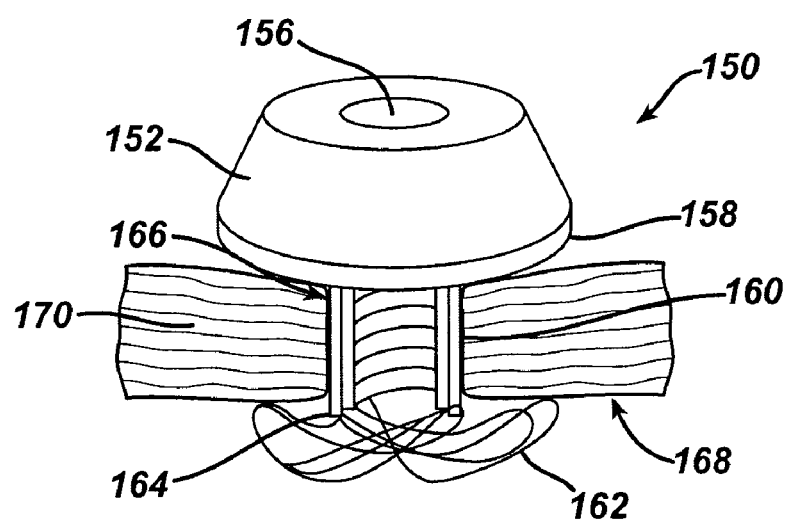
FIG. 4B is a partial cross-sectional view of the device of FIG. 4A shown in a deployed configuration.

Another embodiment of a surgical access device is illustrated in FIGS. 4A and 4B. A surgical access device 150 is provided having a housing 152 with a deployment shaft 154 extending therefrom. The housing 152 can include any number of sealing ports as needed, for example, two, three, four, etc., but in the illustrated embodiment, the housing 152 has a single sealing port 156 extending therethrough with a central longitudinal axis aligned with a central longitudinal axis of the surgical access device 150. The surgical access device 150 can also include a housing base 158 having a cannula 160 extending therefrom. The cannula 160 can include a mesh anchor 162 coupled to a distal end 164 thereof for providing stabilization of the surgical access device 150. The mesh anchor 162 can be disposed inside the cannula 160 during insertion of the cannula 160 into a tissue opening 166. Once the cannula 160 is in position within the tissue opening 166, the deployment shaft 154 can be inserted into the cannula 160 to push the mesh anchor 162 out of the cannula 160. Once the mesh anchor 162 is deployed from the cannula 160, it can expand radially outward from the distal end 164 of the cannula 160 and retroflex proximally against an inner surface 168 of tissue 170 to provide stabilization for the access device 150. The housing 152 can sit flush against the housing base 158, and the deployment device 154 can be positioned within the cannula 160 to provide a working channel through the device 150 through which instruments can be inserted. The mesh anchor 162 can be formed of any suitable material known in the art, including, but not limited to, an elastic material or a shape memory material such as nitinol, and/or other materials such as polypropoleye, polyetholene, nylon, sanoprene, isoplast, isoprene, etc.

Figure 5A:
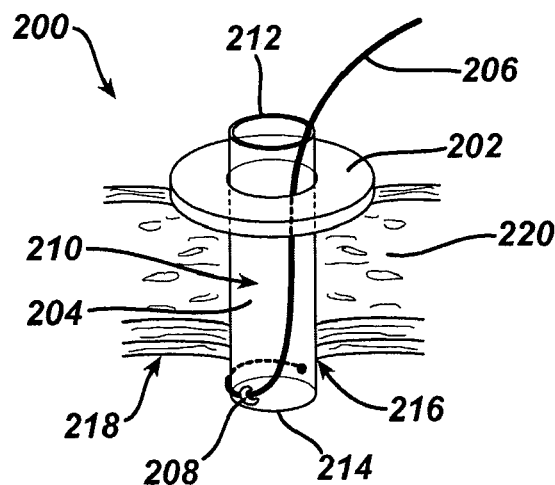
FIG. 5A is a perspective view of an embodiment of an adjustable surgical access device having a wire shown in an insertion configuration.
Figure 5B:
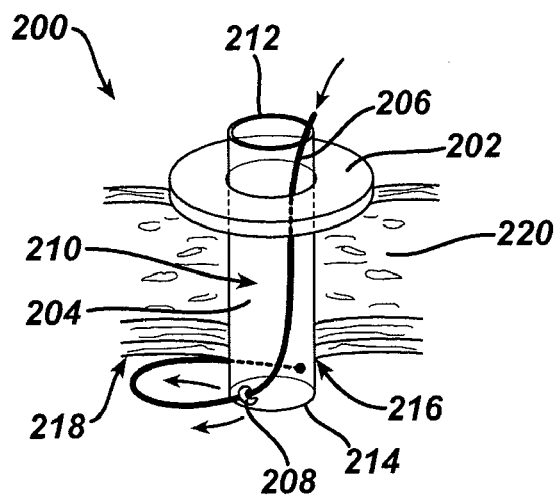
FIG. 5B is a perspective view of the device of FIG. 5A showing the wire in a deployed configuration.
Figure 5B:
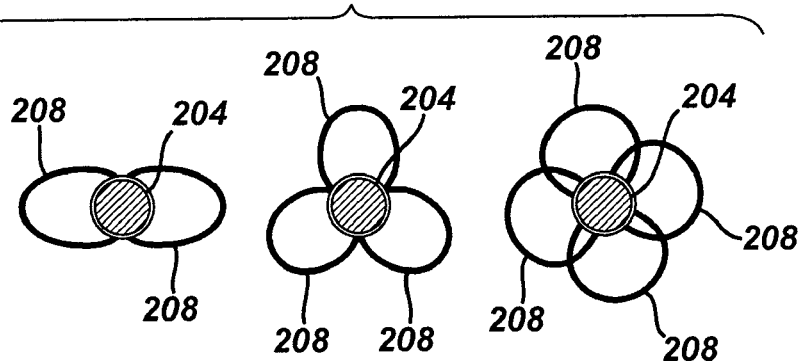

In a further exemplary embodiment illustrated in FIGS. 5A-5C, a surgical access device 200 is provided having a cannula 204 with a housing base 202. As will be appreciate by those skilled in the art, any suitable housing and seal system can be used with the access device 200. The access device 200 can have one or more deployable anchors that can provide anchoring for the access device 200. For example, the access device 200 can include one or more flexible wires 206 that can extend through eye hooks 208 or other restraining mechanisms along a sidewall 210 of the cannula 204. The wire 206 can extend from a proximal end 212 of the cannula 204 to a distal end 214 of the cannula in an insertion configuration, as shown in FIG. 5A. Once the access device 200 is disposed within a tissue opening 216, the wire 206 can be pushed through the eye hook 208 to cause the wire 206 to extend radially outward from the cannula 204 at the distal end 214 of the cannula 204. In some embodiments, two wires 208 can be used to provide two "lobes" extending radially outward from the distal end of the cannula. The lobes can rest against an inner surface 218 of tissue 220 and provide stabilization for the device 200. In other embodiments, three, four, or more wires 208 can be used to extend radially outward from the cannula 204 as shown in FIG. 5C, providing additional stabilization. Once a surgical procedure is complete, the wires 208 can be pulled proximally through the eye hook 208 so that the device 200 can be removed from the opening 216.

In another exemplary embodiment illustrated in FIGS. 6A-6C, a surgical access device 250 is provided having a housing 252 with a cannula 254 extending therefrom. The housing 252 can include any number of sealing ports as needed, for example, two, three, four, etc., but in the illustrated embodiment, the housing 252 has a single sealing port 256 extending therethrough with a central longitudinal axis aligned with a central longitudinal axis of the surgical access device. The housing 252 can be positioned on a housing base 258 and can include an actuator 260 formed therein for controlling movement of the cannula 254, as will be described below. The actuator 260 can rotate relative to the housing 252, the housing base 258, and the cannula 254 by means of a ratchet mechanism 262. A bottom portion of the ratchet mechanism 262 can be disposed on the housing base 258 and a top portion of the ratchet mechanism 262 can be disposed on the rotatable actuator 260.

The cannula 254 can be formed of a flexible material, for example, polypropoleye, polyetholene, nylon, sanoprene, isoplast, isoprene, etc., and can include a plurality of stability rings 264 positioned inside the cannula 254. The stability rings 264 can be circular, substantially rigid structures that are positioned at angles, for example, 45 degree angles, within the cannula 254 when the cannula 254 is in an insertion (reduced diameter) configuration as shown in FIG. 6A. As will appreciated by those skilled in the art, the stability rings 264 can be positioned at any angle within the cannula 254 as needed, including from about 5 degrees to about 175 degrees. The stability rings 264 can give structure to the flexible cannula 254, causing it to maintain a cylindrical shape. In some embodiments, the stability rings 264 can be disposed on an inner surface of the cannula 254. In other embodiments, the cannula 254 can include an inner sheath, and the stability rings 264 can be disposed between the flexible cannula 254 and the inner sheath.

In some embodiments, the stability rings 264 can be connected by a suture 266 that extends from a distal end 268 of the cannula 254 up through the actuator 260. Each stability ring 264 can be connected to the suture 266 on one side thereof, as shown in FIGS. 6A and 6B, or alternatively can be connected to one or more sutures at various locations. As the actuator 260 is rotated, the suture 266 can be wrapped around the actuator 260 causing the suture 266 in the cannula 254 to shorten and to pull up on the distal end 268 of the cannula 254. As the distal end 268 of the cannula 254 moves toward the housing 252, the stability rings 264 can collapse together, and the flexible cannula 254 can expand outward until tissue 270 is engaged, thereby increasing the size of the opening through the tissue.

In use, the access device 250 can be inserted into a tissue opening 272 in the insertion configuration as shown in FIG. 6A. Once within the tissue 270, the actuator 260 can be rotated in a first direction to wind the suture 266 up around the actuator 260 and shorten its length. This causes the suture 266 to pull up on the distal end 268 of the cannula 254, collapsing the flexible cannula 254 and the stability rings 264 against an inner surface 274 of the tissue 270. This anchors the cannula 254 against the tissue 270, providing stability to the access device 250. A slip clutch ratchet mechanism, or other such protection mechanism, can prevent the actuator 260 from over tightening the cannula 254 against the tissue 270. The flexible cannula 254 and the stability rings 264 can bulge outward so that a smooth interior surface is maintained through which an instrument can be inserted during a surgical procedure. Once the procedure is complete, the actuator 260 can be rotated in a second direction to unwind the suture 266 and to relax the flexible cannula 254. As will be appreciated by those skilled in the art, other release mechanisms can be used such as a button on the actuator 260 that releases the suture 266 or a pull tab on the actuator 260 that releases the suture 266. As will be appreciated by those skilled in the art, the first and second directions can generally be in opposite directions and can each be clockwise or counter-clockwise as needed. In the illustrated embodiment, the first direction is in the counter-clockwise direction as shown in FIG. 6B, and the second direction is in the clockwise direction.

In another embodiment illustrated in FIGS. 7A-7D, a surgical access device 300 is provided having a housing base 302, an actuator 304, and a cannula 306 extending from the housing base 302. While a housing is not shown, it will be appreciated by those skilled in the art that any housing known in the art can be used with the surgical access device 300. The cannula 306 can be formed of a flexible material, for example, polypropoleye, polyetholene, nylon, sanoprene, isoplast, isoprene, etc., and can couple to the housing base 302 by any mating mechanism known in the art, including, but not limited to, adhesive, interference fit, fasteners, etc. A distal end 310 of the cannula 306 can include a flexible retention ring 308 disposed therein. The retention ring 308 can have a diameter in the deployed configuration that is greater than a diameter of the flexible cannula 306 such that the distal end 310 of the cannula 306 can flare radially outward toward the retention ring 308.

The access device 300 can include an obturator 322 for inserting the access device 300 into a tissue opening 324 and for retaining the cannula 306 in an insertion configuration. As shown, the obturator 322 can include an elongate body 332 having a sharp tissue penetrating distal end 326 and a rotatable head 328 on its proximal end. Since the retention ring 308 has a diameter greater than a diameter of the cannula 312, insertion into the tissue opening 324 can be hindered by the larger retention ring 308. Accordingly, the obturator 322 can include one or more latches 330 disposed near its distal end 326 that extend radially outward from the elongate body 332 for retaining the retention ring 308 of the cannula 306. The latches 330 hold the retention ring 308 against the body of the obturator 322 such that the radius of the cannula 306 remains constant during insertion. A mechanical or electrical coupling mechanism can be disposed within the obturator 322 between the latches 330 and the rotatable head 328. In this way, the rotatable head 328 of the obturator 322 can be rotated in a first direction to actuate the electrical or mechanical coupling mechanism to cause the latches 330 to retract inside the elongate body 332 and release the retention ring 308 of the cannula 306.

The cannula 306 can also include one or more sutures 312 extending from the retention ring 308 to the actuator 304. In one embodiment, the suture 312 can be embedded in a sidewall of the flexible cannula 306. As the actuator 304 is rotated, the suture 312 is wound around a circular wheel 314 in the actuator 304, causing the suture 312 to shorten. The shortening of the suture 312 pulls up on the retention ring 308 causing the flexible cannula 306 to collapse and pull the ring 308 up toward the housing base 302 until it is secure against an inner surface 316 of the tissue 318. Once secure against the surface 316, the collapsed portion of the cannula 306 can act as an anchor for the access device 300, providing stability thereto. A pull tab 320 extending from the housing base 302 can be connected to the actuator 304 such that pulling on the tab 320 releases the suture 312, thereby relaxing the cannula 306 back to an insertion configuration.

Figure 7A:
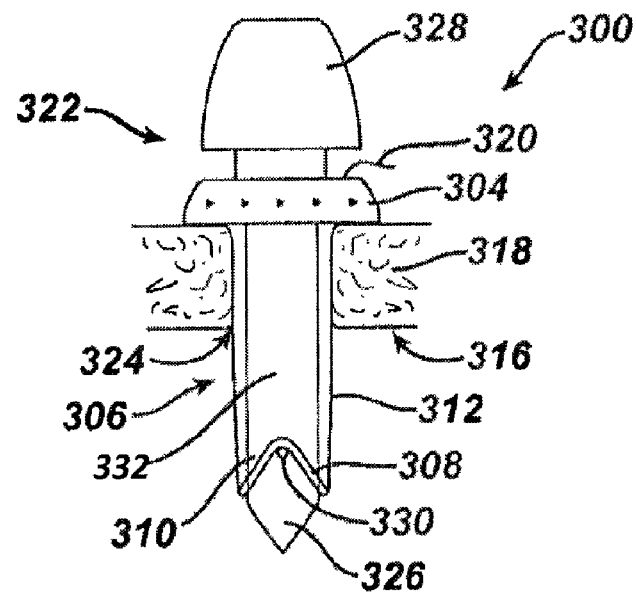
FIG. 7A is a side view of one embodiment of an adjustable surgical access device having an obturator disposed therein for mounting a flexible cannula of the device in an insertion configuration.
Figure 7B:
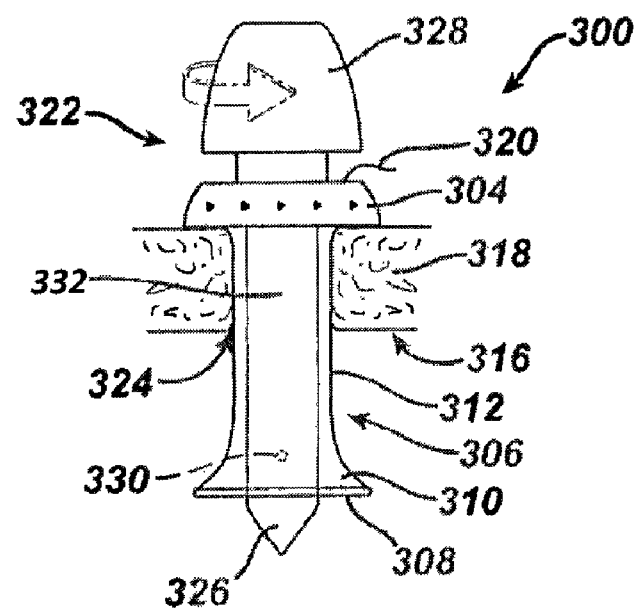
FIG. 7B is a side view of the device of FIG. 7A showing the flexible cannula in which the obturator has released the flexible cannula.
Figure 7C:
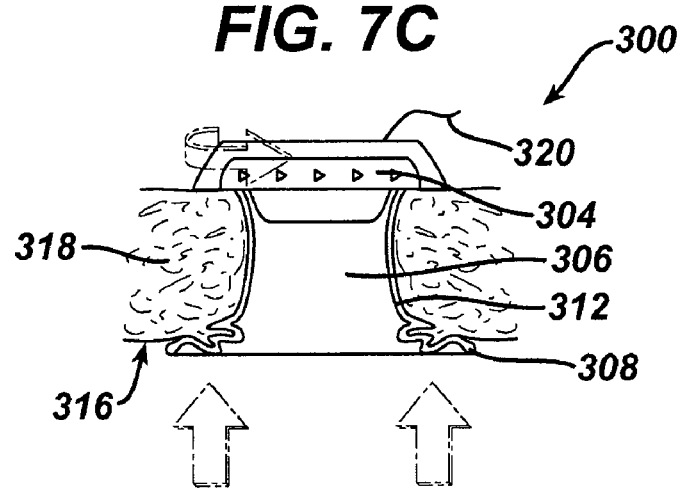
FIG. 7C is a partial cross-sectional view of the device of FIG. 7A in a deployed configuration.
Figure 7D:
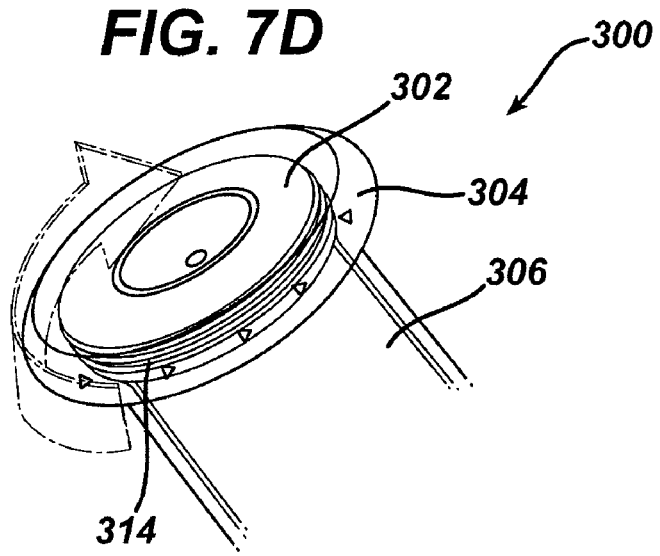
FIG. 7D is a perspective view of an actuator of the device of FIG. 7A.
Figure 7E:
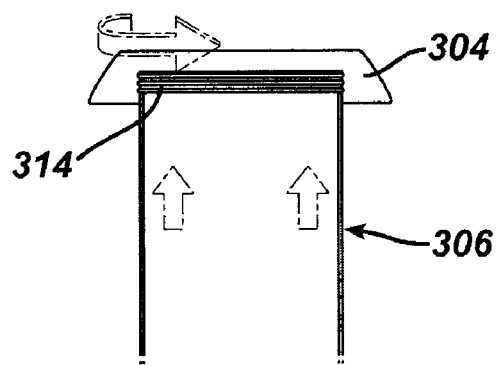
FIG. 7E is a partial cross-sectional view of the actuator of FIG. 7D.

In use, the surgical access device 300 can be inserted into the tissue opening 324 using the obturator 322. The obturator 322 can be disposed inside the cannula 306 and the latches 330 on the obturator 322 can retain the retention ring 308 of the cannula 306, as shown in FIG. 7A. Once inserted inside the tissue 318, the rotatable head 328 of the obturator 322 can be rotated to cause the latches 330 to retract inside the obturator 322, thereby releasing the retention ring 308, as shown in FIG. 7B. The obturator 322 can then be removed from the flexible cannula 306. In order to anchor the cannula 306 against the tissue 318 for stability, the actuator 304 can be rotated in a first direction to tighten the suture 312 and pull up on the retention ring 308 of the cannula 306. This can cause the cannula 306 to collapse and pull the ring 308 against the inner surface 316 of the tissue 318. Once a surgical procedure is completed, the tab 320 can be pulled to release the suture 312, thereby relaxing the cannula 306 and allowing it to return to its insertion configuration for removal from the tissue opening 324.

As will be appreciated by those skilled in the art, any and all of the embodiments disclosed herein can be interchangeable with one another as needed. For example, an exemplary surgical access device kit could include multiple housings and seal bases with one or more cannulas. Various release mechanisms known in the art can be used to releasably attach the various cannulas to a housing.

There are various features that can optionally be included with any and all of the surgical access device embodiments disclosed herein. For example, a component of the device, such as a seal, housing, cannula, etc., can have one or more lights formed thereon or around a circumference thereof to enable better visualization when inserted within a patient. As will be appreciated, any wavelength of light can be used for various applications, whether visible or invisible. Any number of ports can also be included on and/or through the surgical access devices to enable the use of various surgical techniques and devices as needed in a particular procedure. For example, openings and ports can allow for the introduction of pressurized gases, vacuum systems, energy sources such as radiofrequency and ultrasound, irrigation, imaging, etc. As will be appreciated by those skilled in the art, any of these techniques and devices can be removably attachable to the surgical access device and can be exchanged and manipulated as needed.

The embodiments described herein can be used in any known and future surgical procedures and methods, as will be appreciated by those skilled in the art. For example, any of the embodiments described herein can be used in performing a sleeve gastrectomy and/or a gastroplasty, as described in U.S. application Ser. No. 12/242,765 entitled "Surgical Access Device" filed on Sep. 30, 2008; U.S. application Ser. No. 12/242,711 entitled "Surgical Access Device with Protective Element" filed on Sep. 30, 2008; U.S. application Ser. No. 12/242,721 entitled "Multiple Port Surgical Access Device" filed on Sep. 30, 2008; U.S. application Ser. No. 12/242,726 entitled "Variable Surgical Access Device" filed on Sep. 30, 2008; U.S. application Ser. No. 12/242,333 entitled "Methods and Devices for Performing Gastrectomies and Gastroplasties" filed on Sep. 30, 2008; U.S. application Ser. No. 12/242,353 entitled "Methods and Devices for Performing Gastrectomies and Gastroplasties" filed on Sep. 30, 2008; and U.S. application Ser. No. 12/242,381 entitled "Methods and Devices for Performing Gastroplasties Using a Multiple Port Access Device" filed on Sep. 30, 2008, all of which are hereby incorporated by reference in their entireties.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination, e.g., a seal, a housing, a cannula, etc. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, the invention described herein will be processed before surgery. First, a new or used instrument is obtained and if necessary cleaned. The instrument can then be sterilized. In one sterilization technique, the instrument is placed in a closed and sealed container, such as a plastic or TYVEK bag. The container and instrument are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility.

It is preferred that device is sterilized. This can be done by any number of ways known to those skilled in the art including beta or gamma radiation, ethylene oxide, steam, and a liquid bath (e.g., cold soak).

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. An adjustable access device, comprising:
a housing having an adjustable cannula extending distally therefrom, the adjustable cannula being formed of a plurality of fibers woven into a mesh material and being movable between an insertion configuration and a deployed configuration in which a distal portion of the cannula retroflexes upward and radially outward toward a proximal portion of the cannula to form an anchor configured for stabilizing the access device; and
a rotatable actuator disposed on the housing and configured to move the cannula between the insertion configuration and the deployed configuration, wherein the rotatable actuator is, configured to decrease a length of at least some of the plurality of fibers extending from the housing to move the cannula to the deployed configuration.

2. The adjustable access device of claim 1, wherein the cannula is configured to telescope within the housing in the insertion configuration.

3. The adjustable access device of claim 1, wherein the anchor has a diameter greater than a diameter of the proximal portion of the cannula.

4. An adjustable access device, comprising:
a housing;
a cannula formed of a weave of fibers extending distally from the housing, the housing and the cannula defining a working channel extending therethrough for receiving instruments; and
an actuator rotatably disposed on the housing such that rotation of the actuator in a first direction relative to the housing is effective to cause a distal portion of the cannula to retroflex upward and radially outward into a deployed configuration to form a distal anchor to engage tissue, wherein a first group of fibers from the weave of fibers is coupled to the actuator, and a second group of fibers from the weave of fibers is not coupled to the actuator.

5. The adjustable access device of claim 4, wherein the distal anchor includes a distal rim configured to engage tissue when the distal anchor is in the deployed configuration.

6. The access device of claim 4, wherein rotation of the actuator in the first direction is effective to shorten a length of the first group of fibers.

7. The adjustable access device of claim 6, wherein the second group of fibers is configured to maintain an original length when the actuator is rotated in the first direction.

8. The adjustable access device of claim 4, wherein the housing includes multiple sealing ports formed therein.

9. The adjustable access device of claim 4, wherein the actuator is rotatable in a second opposite direction to move the anchor portion of the cannula from the deployed configuration to an insertion configuration in which the cannula has a substantially constant outer diameter.

10. The adjustable access device of claim 4, wherein the cannula is configured to telescope longitudinally through the housing when the actuator is rotated in the first direction.

11. The adjustable access device of claim 4, wherein the anchor portion has a diameter substantially greater than a diameter of the cannula when in the deployed configuration.

12. The adjustable access device of claim 4, further comprising at least one sealing element disposed within the working channel, the at least one sealing element being effective to form at least one of a seal around an instrument inserted through the working channel and a seal across the working channel when no instrument is inserted through the working channel.

* * * * *